US012569253B2

(12) United States Patent
Franklin

(10) Patent No.: US 12,569,253 B2
(45) Date of Patent: Mar. 10, 2026

(54) INFLATION HUB FOR A FLUID INFLATABLE APPARATUS

(71) Applicant: Prytime Medical Devices, Inc., Boerne, TX (US)

(72) Inventor: Curtis J. Franklin, Lakewood, CO (US)

(73) Assignee: PRYTIME MEDICAL DEVICES, INC., Boerne, TX (US)

( * ) Notice: Subject to any disclaimer, the term of this patent is extended or adjusted under 35 U.S.C. 154(b) by 398 days.

(21) Appl. No.: 18/015,658

(22) PCT Filed: Jul. 16, 2021

(86) PCT No.: PCT/US2021/042067
§ 371 (c)(1),
(2) Date: Jan. 11, 2023

(87) PCT Pub. No.: WO2022/016109
PCT Pub. Date: Jan. 20, 2022

(65) Prior Publication Data
US 2023/0248367 A1      Aug. 10, 2023

Related U.S. Application Data

(60) Provisional application No. 63/052,786, filed on Jul. 16, 2020.

(51) Int. Cl.
*F16K 5/04*           (2006.01)
*A61B 17/12*          (2006.01)
(Continued)

(52) U.S. Cl.
CPC .. *A61B 17/12136* (2013.01); *A61B 17/12109* (2013.01); *F16K 5/0407* (2013.01); *F16K 17/0406* (2013.01); *A61M 25/10186* (2013.11)

(58) Field of Classification Search
CPC .. A61M 5/16877–16895; A61M 5/504; A61M 2005/5046–506; A61M 25/0097;
(Continued)

(56) References Cited

U.S. PATENT DOCUMENTS

| | | |
|---|---|---|
| 3,467,101 A | 9/1969 | Raible et al. |
| 4,439,185 A | 3/1984 | Lundquist |

(Continued)

FOREIGN PATENT DOCUMENTS

| | | |
|---|---|---|
| EP | 0368523 A2 | 5/1990 |
| EP | 0492361 A1 | 7/1992 |

(Continued)

OTHER PUBLICATIONS

Scott et al., A novel fluoroscopy-free, resuscitative endovascular aortic balloon occlusion system in a model of hemorrhagic shock, The Journal of Trauma and Acute Care Surgery, vol. 75, Issue 1 (Jul. 2013).

(Continued)

*Primary Examiner* — Elizabeth Houston
*Assistant Examiner* — Jonathan A Hollm
(74) *Attorney, Agent, or Firm* — Panitch Schwarze Belisario & Nadel LLP

(57) ABSTRACT

An inflation hub includes a body having an internal lumen defining first and second lumen sections. A stopcock valve has a stem extending from the body between the first and second lumen sections, the stem being selectively rotatable between an open position, wherein an internal channel thereof fluidly connects the first and second lumen sections together, and a closed position, wherein the stopcock valve fluidly disconnects the first and second lumen sections from one another. A pressure-relief valve is integrated within the stem of the stopcock valve and in fluid communication with the internal channel thereof, and includes a loading member (Continued)

biasing the pressure-relief valve into a closed position. The pressure-relief valve moves into an open position when the stopcock valve is in the open position thereof and a pressure with the internal lumen of the body exceeds a threshold, opening pressure of the loading member.

20 Claims, 8 Drawing Sheets

(51) Int. Cl.
  *A61M 25/10*        (2013.01)
  *F16K 17/04*        (2006.01)

(58) Field of Classification Search
  CPC ... A61M 25/0026–003; A61M 25/1018–1025;
      A61M 2025/102–1022; A61M 39/22–26;
      A61M 2039/222–268; A61M 2039/229;
      A61M 1/78–785; A61M 16/20–209;
      F16K 5/00–227; F16K 17/003–42
  See application file for complete search history.

(56) References Cited

U.S. PATENT DOCUMENTS

| | | | |
|---|---|---|---|
| 4,573,470 | A | 3/1986 | Samson et al. |
| 4,582,181 | A | 4/1986 | Samson |
| 4,616,653 | A | 10/1986 | Samson et al. |
| 4,646,719 | A | 3/1987 | Neuman et al. |
| 4,838,268 | A | 6/1989 | Keith et al. |
| 4,838,269 | A | 6/1989 | Robinson et al. |
| 4,846,174 | A | 7/1989 | Willard et al. |
| 4,906,241 | A | 3/1990 | Noddin et al. |
| 5,032,113 | A | 7/1991 | Burns |
| 5,042,985 | A | 8/1991 | Elliott et al. |
| 5,087,246 | A | 2/1992 | Smith |
| 5,380,284 | A | 1/1995 | Don Michael |
| 5,387,225 | A | 2/1995 | Euteneuer et al. |
| 5,607,394 | A | 3/1997 | Andersen et al. |
| 5,779,731 | A | 7/1998 | Leavitt |
| 6,129,737 | A | 10/2000 | Hamilton et al. |
| 6,368,301 | B1 | 4/2002 | Hamilton et al. |
| 7,468,027 | B2 | 12/2008 | Barbut et al. |
| 8,066,667 | B2 | 11/2011 | Hayman et al. |
| 8,088,121 | B2 | 1/2012 | Nishide et al. |
| 8,267,871 | B2 | 9/2012 | Eberhardt et al. |
| 8,486,046 | B2 | 7/2013 | Hayman et al. |
| 8,491,648 | B2 | 7/2013 | Hassan et al. |
| 8,888,740 | B2 | 11/2014 | Barbut et al. |
| 9,131,874 | B2 | 9/2015 | Eliason et al. |
| 9,498,225 | B2 | 11/2016 | Zhadkevich |
| 9,731,099 | B2 | 8/2017 | Krolik et al. |
| 10,004,622 | B2 | 6/2018 | Sanati et al. |
| 2007/0167972 | A1 | 7/2007 | Euteneuer et al. |
| 2007/0219466 | A1 | 9/2007 | Tremulis et al. |
| 2008/0188803 | A1 | 8/2008 | Jang |
| 2008/0312609 | A1* | 12/2008 | Miller .................... A61B 90/92 |
| | | | 604/272 |
| 2009/0275919 | A1 | 11/2009 | Todd et al. |
| 2010/0204712 | A1* | 8/2010 | Mallaby ................. A61B 17/22 |
| | | | 606/128 |
| 2014/0018746 | A1* | 1/2014 | Ueda ................... A61M 39/223 |
| | | | 604/248 |
| 2015/0013807 | A1* | 1/2015 | Ueda ................... F16K 11/0856 |
| | | | 137/625.47 |
| 2015/0133892 | A1 | 5/2015 | Joe et al. |

FOREIGN PATENT DOCUMENTS

| | | |
|---|---|---|
| WO | 2006115904 A2 | 11/2006 |
| WO | 2011133736 A2 | 10/2011 |
| WO | 2014036530 A1 | 3/2014 |

OTHER PUBLICATIONS

Park et al., Resuscitative Endovascular Balloon Occlusion of the Aorta (REBOA): Comparison With Immediate Transfusion Following Massive Hemorrhage in Swine, WTA 2015 Plenary Paper, J. Trauma Acute Care Surg, vol. 79, No. 6 (Feb. 27, 2015).

Neuzil et al., Balloon technology for catheter ablation of atrial fibrillation, Cor et Vasa 54, E401-E407 (2012).

Spiotta et al., Balloon remodeling for aneurysm coil embolization with the coaxial lumen Scepter C balloon catheter: initial experience at a high vol. center, J. NeuroIntervent Surg 2013, 5:582-585 (Nov. 7, 2012).

Tokai Medical Products Co., TMP Lock Balloon Catheter Set Product Insert (Oct. 18, 2013).

Gerstenfeld et al., Pulmonary vein isolation using a compliant endoscopic, Springer Science+Business Media, LLC (2010).

Deaton, Image-Guided Thrombectomy in Vascular Surgery, Endovascular Today (Jul. 2005).

Mathis, et al., Physicalcharacteristics of Balloon Catheter Systems Used in Temporary Cerebral Artery Occlusion, Amercian Society of Neuroradiology (Nov. 1994).

Gu et al., A New Technique for Sizing of Atrial Septal Defects, Catheterization and Cardiovascular Interventions, Jan. 1999.

Saab, Applications of High-Pressure Balloons in the Medical Device Industry , Medical Device & Diagnostic Industry Magazine, Sep. 2000.

Chengod, et al., Selective Left Bronchial Intubation and Left-Lung Isolation in Inffants and Toddlers: Analysis of a New Technique, Department of Anesthesiology and Intensive Care, Division of Cardiothoracic and Vascular Anesthesiology and Intensive Care, Amrita Institute of Medical Sciences and Research Center, Kerala, India, . of Cardiothoracic and Vascular Anesthesia, vol. 19, No. 5, at 636-41 (Oct. 2005).

Gal et al., First Dutch experience with the endoscopic laser balloon ablation system for the treatment of atrial fibrillation, Neth Heart J (2015) 23 :96-99 (Nov. 12, 2014).

Metzner et al., One-year clinical outcome after pulmonary vein isolation using the novel endoscopic ablation system in patients with paroxysmal atrial fibrillation, Heart Rhythm, vol. 8, No. 7 (Jul. 2011).

Phillips et al., Anatomic Location of Pulmonary Vein Electrical Disconnection with Balloon-Based Catheter Ablation, Journal of Cardiovascular Electrophysiology, vol. 19, No. 1 (Jan. 2008).

International Report on Patentability issued Jan. 26, 2023 in International Application No. PCT/US2021/042067.

* cited by examiner

INFLATION HUB FOR A FLUID INFLATABLE APPARATUS

CROSS-REFERENCE TO RELATED APPLICATIONS

This application is a Section 371 of International Application No. PCT/US2021/042067, filed Jul. 16, 2021, which was published on Jan. 20, 2022, under International Publication No. WO 2022/016109 A1, which claims priority to U.S. Provisional Patent Application No. 63/052,786, filed Jul. 16, 2020, the contents of each of which are incorporated herein by reference in their entireties.

BACKGROUND OF THE DISCLOSURE

The disclosure relates to an inflation hub for a fluid inflatable apparatus, such as, for example, for a medical catheter.

Conventional medical catheters 5 may include an inflatable balloon 7 configured to perform partial and full occlusion of a patient's vessel, such as, for example, at various locations in the patient's aorta, including the descending thoracic aorta and the abdominal aorta. Generally, as shown in FIGS. 1 and 2, the inflatable occlusion balloon 7 is fluidly connected with an outlet of an inflation hub 2 via a catheter shaft 4 defining an internal lumen. The inflation hub 2 generally includes a valve 3, e.g., a stopcock, that is oriented in an open position (FIGS. 1, 2) to permit the flow of fluid therethrough during balloon inflation, and oriented in the closed position (now shown) thereafter to maintain balloon inflation. The inflation hub 2 may further include a pressure-relief valve 6 fluidly connected to the catheter shaft 4. The pressure-relief valve 6 defines a cracking pressure set to prevent overinflation of the balloon. Often, as shown in FIGS. 1 and 2, the pressure-relief valve 6 is positioned adjacent to, and in series with, the stopcock 3 via a molded pressure relief fitting, bonding or the like. One drawback of such a design is that the inflation hub 2 is long, thereby being increasingly susceptible to fracture from bending. Another drawback is that the inflation hub 2 is formed of two separate components requiring manufacture.

It would, therefore, be advantageous to manufacture a more compact inflation hub formed of a single component to improve reliability and ease of manufacture thereof.

BRIEF SUMMARY OF THE DISCLOSURE

Briefly stated, an aspect of the present disclosure is directed to an inflation hub for attachment to a fluid inflatable apparatus. The inflation hub includes a body having an internal lumen defining a first lumen section and a second lumen section, an inlet of the first lumen section being configured for connection to an inflation device, and an outlet of the second lumen section being configured for connection to the fluid inflatable apparatus. A stopcock valve has a stem angularly extending from a portion of the body between the first lumen section and the second lumen section of the internal lumen, the stem being selectively rotatable between an open position, wherein an internal channel of the stem fluidly connects the first lumen section with the second lumen section, and a closed position, wherein the stopcock valve fluidly disconnects the first lumen section from the second lumen section. A pressure-relief valve is integrated within the stem of the stopcock valve and in fluid communication with the internal channel thereof, the pressure-relief valve including a loading member biasing the pressure-relief valve into a closed position thereof. The pressure-relief valve is configured to move into an open position thereof when the stopcock valve is in the open position thereof and a pressure with the internal lumen of the body exceeds a threshold, opening pressure of the loading member.

In one configuration, the stopcock valve further includes a stopcock valve body angularly extending from the internal lumen of the body, and the stem is sealing and rotationally received within the valve body. In such a configuration, the stopcock valve body may be monolithic with the body.

In any of the previous configurations, the internal channel of the stem may have a generally lateral channel portion and a generally axial channel portion in fluid communication with and angularly extending therefrom. In such a configuration, the generally lateral channel portion of the stem may be interposed between, and in line with, the first lumen section and the second lumen section in the open position of the stopcock valve. In such a configuration. the generally lateral channel portion of the stem may additionally or alternatively be interposed between, and angularly offset from, the first lumen section and the second lumen section in the closed position of the stopcock valve.

In any of the previous configurations, the stem of the stopcock valve may be selectively rotatable between only two operative positions, the open position thereof being a first of the two operative positions and the closed position thereof being a second of the two operative positions.

In any of the previous configurations, the stem of the stopcock valve may be rotatable substantially 90° between the open position thereof and the closed position thereof.

In any of the previous configurations, the pressure-relief valve may further include a valve body sealingly mounted to the stem, the valve body having an internal valve body channel in fluid communication with the internal channel of the stem; a valve seat within the internal valve body channel; and a movable valve member sealingly engaged with the valve seat by the loading member in the closed position of the pressure-relief valve. In such a configuration, the valve body of the pressure-relief valve may further include at least one vent port fluidly communicating the internal valve body channel with external atmosphere, the at least one vent port being fluidly disconnected from the internal channel of the stem by the engagement of the movable valve member with the valve seat in the closed position of the pressure-relief valve and the at least one vent port being fluidly communicated with the internal channel of the stem in the open position of the pressure-relief valve. Additionally, or alternatively, in such a configuration, the valve member may be a ball.

In any of the previous configurations, the loading member may be a spring.

In any of the previous configurations, wherein the threshold, opening pressure of the loading member may be approximately 6 psi.

In any of the previous configurations, the stopcock valve may further include a handle laterally extending from the stem, whereby rotation of the handle is configured rotate the stem.

In any of the previous configurations, an upper rim of the stopcock valve may include at least one recess permitting fluid travel therethrough.

In any of the previous configurations, the inflation hub may be combined with a medical catheter, wherein the fluid inflatable apparatus is the medical catheter, the medical catheter including an inflatable occlusion balloon fluidly connected with a catheter shaft, the catheter shaft being selectively connectable with the outlet of the second lumen section.

Another aspect of the present disclosure is directed to a method of using any of the previous configurations of the inflation hub. The method includes the steps of connecting the fluid inflatable apparatus with the outlet of the second lumen section; and inflating the fluid inflatable apparatus from the inlet of the first lumen section.

In one configuration, the method may further include the step of rotating the stem into the open position thereof before the inflating step, thereby fluidly connecting the first lumen section with the second lumen section through the internal channel of the stem.

In any of the previous configurations, the inflating step may include inflating the fluid inflatable apparatus to a pressure greater than the threshold, opening pressure of the loading member, thereby moving the pressure-relief valve into the open position thereof.

In any of the previous configurations, method may further include the step of rotating the stem into the closed position thereof.

BRIEF DESCRIPTION OF THE SEVERAL VIEWS OF THE DRAWINGS

The following description of an embodiment of the disclosure will be better understood when read in conjunction with the appended drawings. It should be understood, however, that the disclosure is not limited to the precise arrangements and instrumentalities shown. In the drawings.

DETAILED DESCRIPTION OF THE DISCLOSURE

Figure 1:
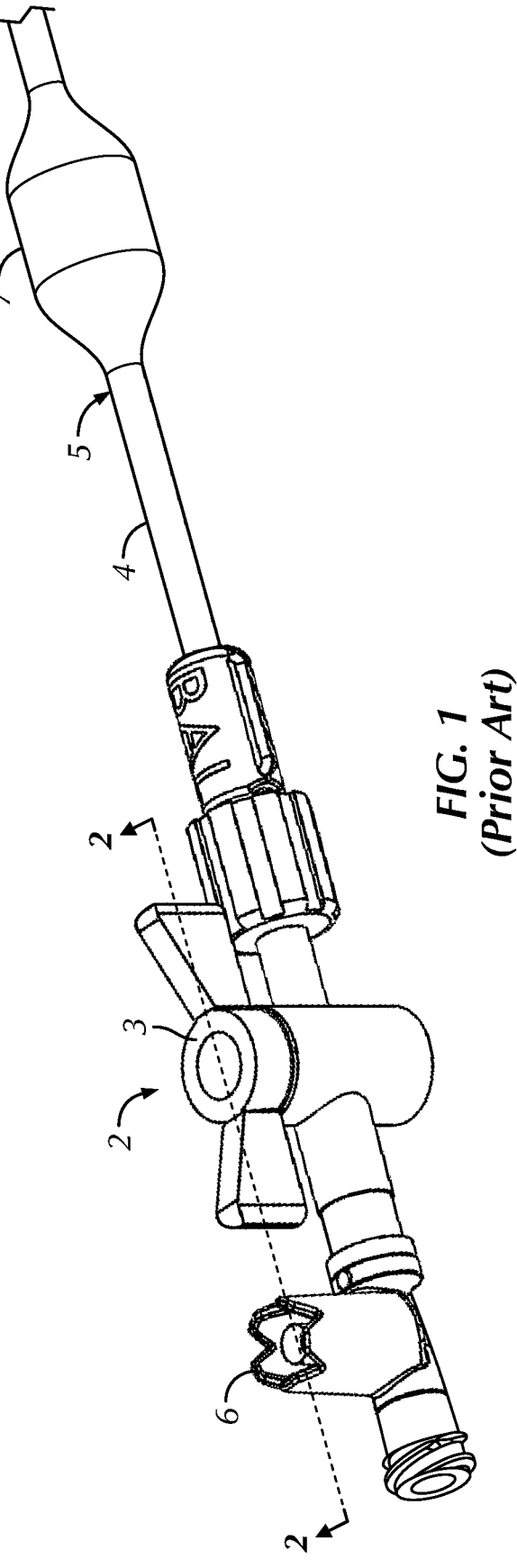
FIG. 1 is a perspective view of a prior art inflation hub connected to a fluid inflatable apparatus.
Figure 2:
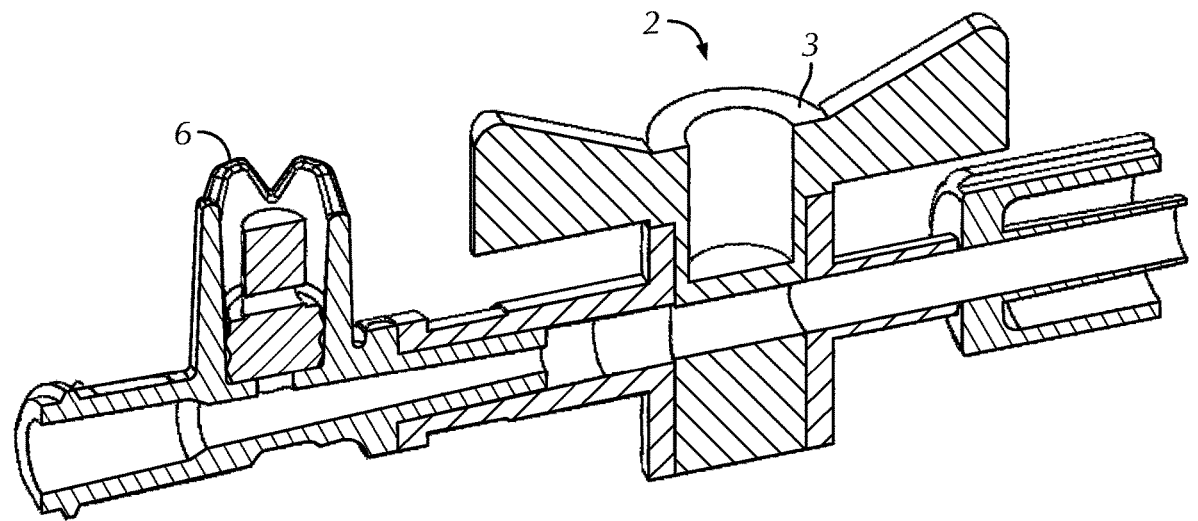
FIG. 2 is a cross-sectional perspective view of the prior art inflation hub of FIG. 1, taken along sectional line 2-2 of FIG. 1.

Certain terminology is used in the following description for convenience only and is not limiting. The words "lower," "bottom," "upper" and "top" designate directions in the drawings to which reference is made. The words "inwardly," "outwardly," "upwardly" and "downwardly" refer to directions toward and away from, respectively, the geometric center of the stopcock, and designated parts thereof, in accordance with the present disclosure. Unless specifically set forth herein, the terms "a," "an" and "the" are not limited to one element, but instead should be read as meaning "at least one." The terminology includes the words noted above, derivatives thereof and words of similar import.

It should also be understood that the terms "about," "approximately," "generally," "substantially" and like terms, used herein when referring to a dimension or characteristic of a component of the disclosure, indicate that the described dimension/characteristic is not a strict boundary or parameter and does not exclude minor variations therefrom that are functionally similar. At a minimum, such references that include a numerical parameter would include variations that, using mathematical and industrial principles accepted in the art (e.g., rounding, measurement or other systematic errors, manufacturing tolerances, etc.), would not vary the least significant digit.

Referring to the drawings in detail, wherein like numerals indicate like elements throughout, there is shown in FIGS. 3-9 an inflation hub, generally designated 10, for attachment to (and fluid communication with) a fluid, i.e., liquid or gas, inflatable apparatus, such as, for example, without limitation, a medical catheter 5, in accordance with an embodiment of the present disclosure. As shown, the inflation hub 10 includes a single body 12 having an inlet 12$a$, an outlet 12$b$ and an internal lumen 12$c$ extending therebetween. The inlet 12$a$ is selectively connectable with an inflation device (not shown) and the outlet 12$b$ is selectively connectable with the fluid inflatable apparatus. In the illustrated configuration, the inlet 12$a$ takes the form of a female luer fitting and the outlet 12$b$ takes the form of a male luer fitting, but the disclosure is not so limited. Rather, the inlet and outlet 12$a$, 12$b$ may take the form of any leakproof connection fittings currently known or that later becomes known. As also should be understood by those of ordinary skill in the art, the body 12 of the inflation hub 10 may include more than one inlet and/or more than one outlet, selectively fluidly connectable with one another.

A stopcock type valve 14 extends angularly, e.g., transversely, from a portion of the body 12 between the inlet 12$a$ and the outlet 12$b$ thereof. The stopcock valve 14 defines a stopcock valve body 14$a$ angularly extending, e.g., generally orthogonally, from the internal lumen 12$c$. In the illustrated embodiment, the stopcock valve body 14$a$ is generally cylindrical, but the disclosure is not so limited. The stopcock valve body 14$a$ is fixed, i.e., stationary, relative to the body 12 of the inflation hub 10. In one configuration, the stopcock valve body 14$a$ may be monolithic with the body 12 of the inflation hub 10. A stopcock stem 14$b$ extends into the valve body 14$a$ in a substantially mating fit therewith. In one configuration, the stopcock stem 14$b$ may form an interference fit with the valve body 14$a$. The stopcock stem 14$b$ includes a stopcock handle 14$c$, e.g., a wing-like handle, proximate an upper end thereof for selectively rotating the stem 14$b$ relative to the valve body 14$a$, as will be described in further detail.

Figure 4:
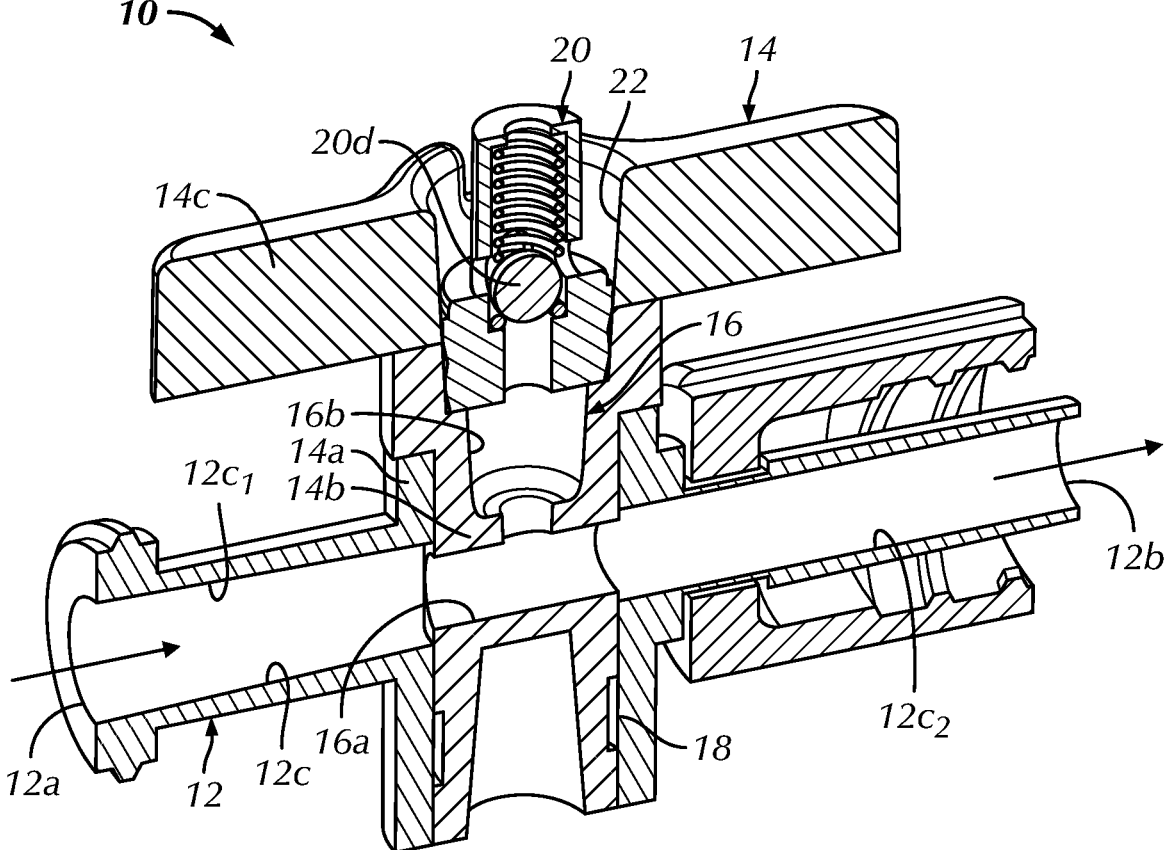
FIG. 4 is a cross-sectional elevational view of the inflation hub of FIG. 3, taken along sectional line 4-4 of FIG. 3.
Figure 6:
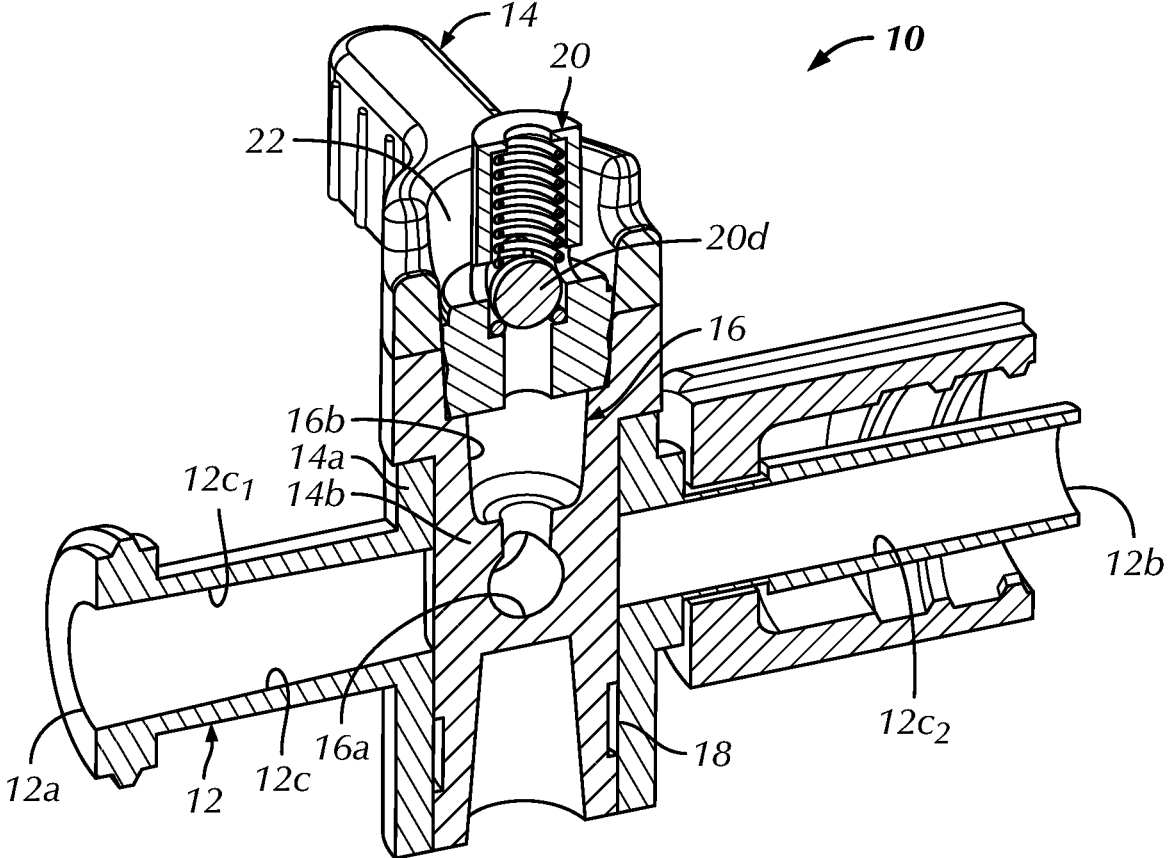
FIG. 6 is a cross-sectional perspective view of the inflation hub of FIG. 5, taken along sectional line 6-6 of FIG. 5.

As shown best in FIGS. 4 and 6, the stopcock stem 14$b$ defines an internal, inverted generally T-shaped channel 16, having a generally lateral channel 16$a$ and a generally axial channel 16$b$ in fluid communication therewith and extending therefrom. The generally axial channel 16$b$ may extend substantially along a central axis of the stopcock stem 14$b$. The lateral channel 16$a$ extends angularly, such as substantially orthogonally, relative to the axial channel 16$b$ and is elevationally aligned with the internal lumen 12$c$ of the inflation hub body 12.

Figure 3:
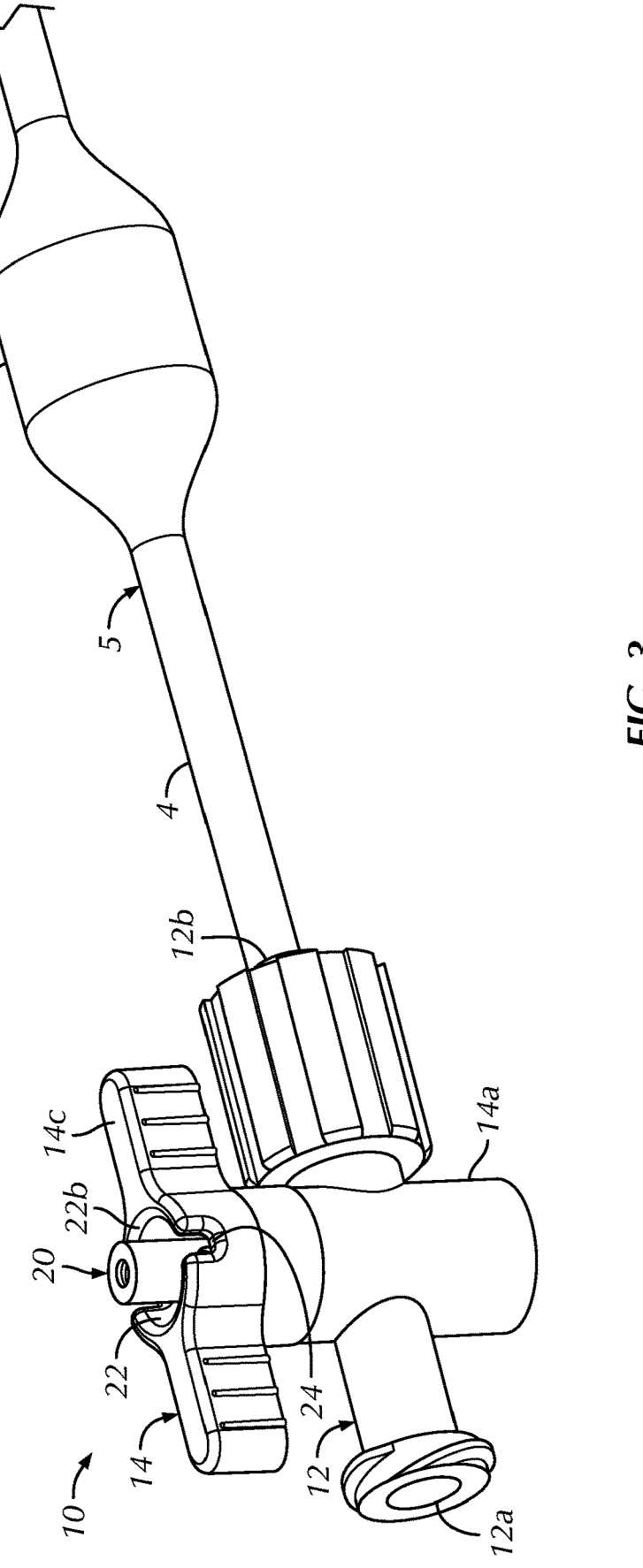
FIG. 3 is a perspective view of an inflation hub according to an embodiment of the present disclosure, with a stopcock valve thereof in an open position.
Figure 5:
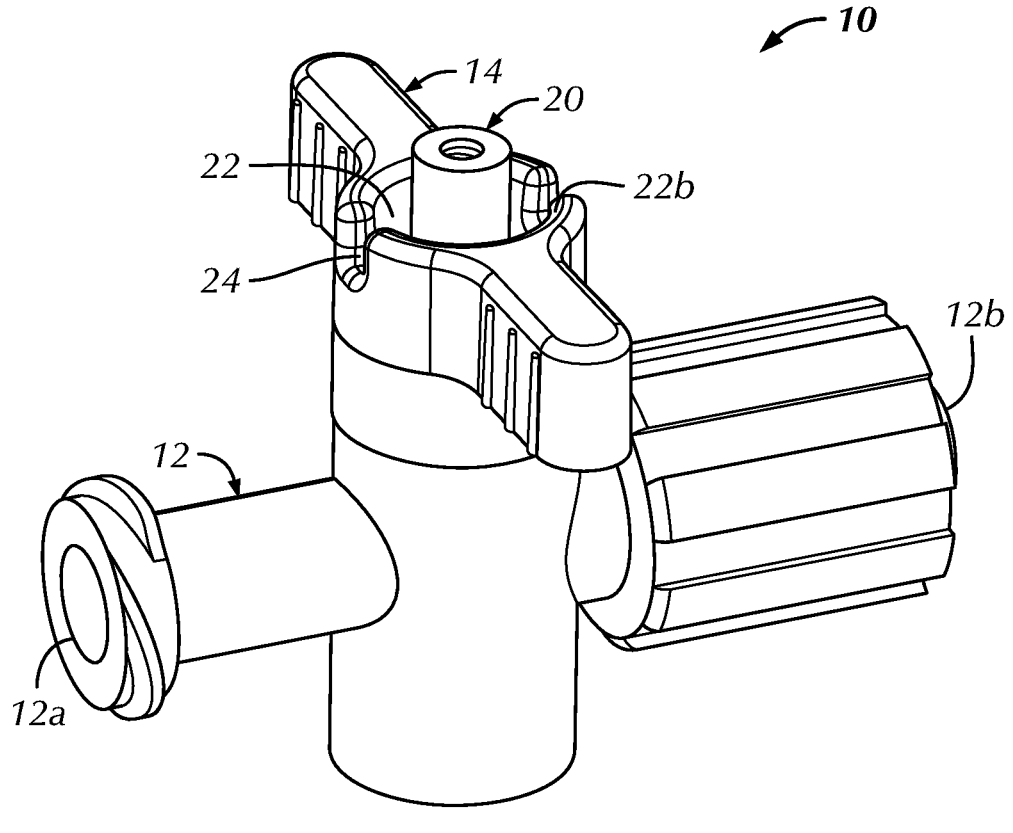
FIG. 5 is a perspective view of the inflation hub of FIG. 1, with the stopcock valve thereof in a closed position.
Figure 7:
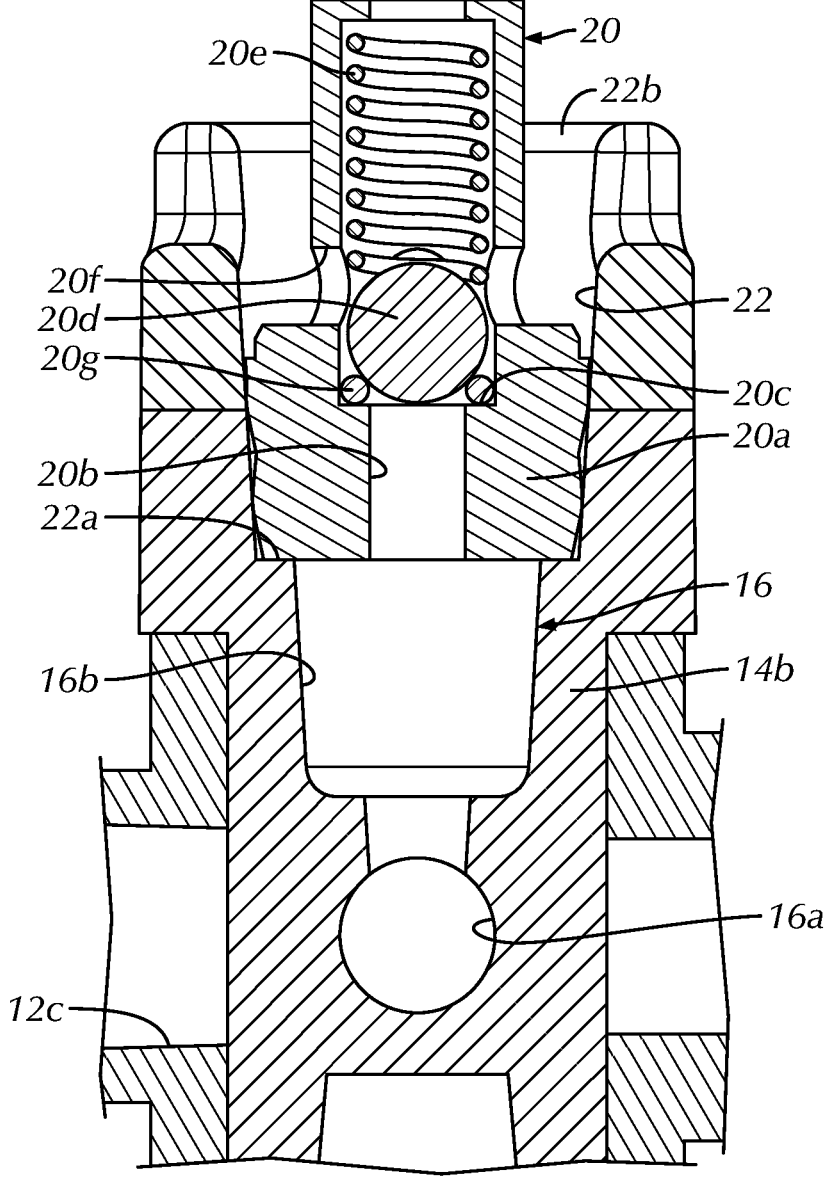
FIG. 7 is an enlarged, elevational partial view of the cross-sectional view of FIG. 6.

The stopcock stem 14$b$ is selectively movable (via the handle 14$c$) between two operative positions. In the illustrated configuration, the stopcock stem 14$b$ is rotatable substantially 90° (quarter-turn), between the two operative positions, but the disclosure is not so limited. For example, without limitation, the stopcock stem 14*b* may be reciprocally translatable or the like between the two operative positions. In an open position (the first operative position), as shown in FIGS. 3-4, the stem 14*b* is positioned such that the lateral channel 16*a* is in line, and in fluid communication, with the internal lumen 12*c*. That is, the lateral channel 16*a* is interposed between a first section 12*cl* of the internal lumen 12*c* and a second section 12*c*2 of the internal lumen 12*c* and fluidly communicates the first and second sections 12*c*1, 12*c*2 of the internal lumen 12*c* with one another. Thus, fluid may flow completely through the internal lumen 12*c*, between the inlet 12*a*, the first section 12*c*1, the lateral channel 16*a*, the second section 12*c*2 and the outlet 12*b* (and ultimately to the fluid inflatable apparatus, such as the catheter shaft 4). In a closed position (the second operative position), as shown in FIGS. 5-7, the stem 14*b* is rotated about an axial axis thereof (compared to the position thereof in the first operative position) such that the lateral channel 16*a* is offset/misaligned from the first and second sections 12*c*1, 12*c*2 of the internal lumen 12. For example, the lateral channel 16*a* may be oriented perpendicularly relative to the internal lumen 12*c*, and, therefore, relative to the direction of fluid flow. Thus, the stopcock type valve 14 fluidly disconnects the first and second sections 12*c*1, 12*c*2 of the internal lumen 12 from one another and substantially prevents fluid flow between the inlet 12*a* and the outlet 12*b* of the inflation hub 12 in the closed position, and fluidly connects the first and second sections 12*c*1, 12*c*2 with one another and permits fluid flow between the inlet 12*a* and the outlet 12*b* of the inflation hub 12 in the open position. As should be understood by those of ordinary skill in the art, however, the stopcock stem 14*b* may be selectively rotatable between more than two operative positions in a manner well understood, e.g., if the body 12 includes more than one outlet, selectively fluidly communicating the inlet 12*a* with a respective one or more of the outlets. Optionally, the stopcock valve 14 may further include a sealing member 18, e.g., an O-ring, positioned between the stopcock valve body 14*a* and stopcock stem 14*b* on an opposite side of the internal lumen 12*c* from the channel 16.

The stopcock type valve 14 further includes a pressure-relief valve 20 integrated within the stopcock stem 14*b*. In the illustrated configuration, and as shown best in FIG. 7, the pressure-relief valve 20 is seated proximate an upper end of the stem 14*b*, within a socket 22 in the stopcock handle 14*c*. Alternatively, the pressure-relieve valve 20 may be positioned entirely within the stem 14*b*. Advantageously, integrating the pressure-relief valve 20 within the stopcock valve 14 results in a more compact inflation hub 12, formed of less pieces, requiring less assembly/bonds, and thereby being more reliable and less prone to fracture.

In the illustrated embodiment, the pressure-relief valve 20 includes a valve body 20*a* mounted upon a base 22*a* of the socket 22. The valve body 20*a* includes an internal valve body channel 20*b* in fluid communication with the channel 16 of the stopcock stem 14*b*. The valve body 20*a* defines an internal valve seat 20*c* in the form of a radially inwardly projecting shoulder. Stated differently, the valve body channel 20*b* defines a step down in width/diameter between an upper portion and a lower portion, forming the inwardly projecting shoulder 20*c* therebetween. A movable valve member 20*d*, e.g., a disc or ball, is disposed within the valve body channel 20*b*, i.e., within the wider portion of the valve body channel 20*b*, and biased against the valve seat 20*c* by a loading member 20*e*, e.g., a spring, disposed with the valve body channel 20*b* to maintain the valve 20 in a closed position. That is, the loading member 20*e* may be interposed between the valve member 20*d* and a terminal end of the valve body channel 20*b*. A sealing member 20*g*, e.g., an O-ring or other sealing seat ring, may form a component of the valve seat 20*c* or be interposed between the valve member 20*d* and the valve seat 20*c* to enhance sealing when the pressure-relief valve 20 is closed.

The load, i.e., force, applied by the loading member 20*e* upon the valve member 20*d* determines the pressure required to open the relief valve 20, i.e., to disengage the valve member 20*d* from the valve seat 20*c*. The cracking, i.e., opening, pressure of the pressure-relief valve 20 defines a threshold pressure for safe inflation of a fluid inflatable apparatus, e.g., without limitation, a medical catheter 5, thereby preventing dangerous overinflation or over-pressurization of a component, such as a balloon or occlusion balloon positioned downstream of the outlet 12*b*. In one configuration, the cracking, i.e., opening, pressure of the loading member 20*e*, and, thus, of the valve 20, may be approximately 0.5 atm (approximately 6 psi), but the disclosure is not so limited. As should be understood by those of ordinary skill in the art, the loading member may take the form of any member capable of storing and releasing energy. The valve body 20*a* further includes at least one side vent port 20*f*, fluidly communicating the valve body channel 20*b* with the external atmosphere. Generally, the vent port(s) 20*f* is positioned on an opposite side of the valve member 20*d*, and thereby sealingly disconnected, from the stopcock stem channel 16 when the pressure-relief valve 20 is in the closed position. When the pressure-relief valve 20 is opened, the side vent port(s) 20*f* becomes fluidly communicated with the stopcock stem channel 16. Thus, pressure within the inflation hub 12, and, therefore, within the line may be vented to the atmosphere, via the stopcock stem channel 16, the pressure-relief valve body channel 20*b* and out the side vent port(s) 20*f*. As should be understood by those of ordinary skill in the art, the pressure-relief valve 20 may alternatively take the form of any other safety valve, currently known, or that later becomes known, capable of integration with the stopcock valve 14 and functioning as described with respect to the pressure-relief valve 20 herein.

In operation, e.g., without limitation, with an occlusion balloon catheter 5, the outlet 12*b* of the inflation hub 12 is connected with the occlusion balloon catheter and the inlet 12*a* of the inflation hub is connected with an inflation device (not shown), e.g., a syringe or the like. The stopcock valve 14 is then rotated into the open position thereof (as previously described), to fluidly communicate the inflation device with the occlusion balloon catheter 5 via the internal lumen 12*c* and the interposed, aligned lateral channel 16*a*. In the open position of the stopcock valve 14, the pressure-relief valve 20 is also fluidly communicated with the inflation hub lumen 12*c*, and, in turn, with the occlusion balloon catheter 5.

The occlusion balloon of the occlusion balloon catheter 5 is then inflated. Should the occlusion balloon be inadvertently overinflated by the user, e.g., to a pressure greater than the cracking pressure of the pressure-relief valve 20, the pressure within the inflation hub 12 will bias the pressure-relief valve 20 open to vent out the overpressure through the side vent port(s) 20*f*. After inflation of the occlusion balloon catheter 5 is completed, the stopcock valve 14 is rotated to the closed position thereof, thereby isolating, i.e., fluidly disconnecting, the pressure-relief valve 20 so that it is no longer in fluid communication with the occlusion balloon of the occlusion balloon catheter 5. Advantageously, isolating the pressure-relief valve 20 from the pressure within the occlusion balloon catheter during use prevents the potential for leaking from the valve 20 over extended use.

Optionally, the upper rim 22*b* of the socket 22, the stem 14*b* or the stopcock valve 14 generally may include at least one recess 24 to ensure that fluid may escape out of the socket 22 via the recess(es) 24, even if an object, e.g., a user's finger, obstructs the open upper end of the socket 22. Additionally, or alternatively, the upper rim 22*b* of the socket 22 or the stopcock valve 14 generally may also project further upwardly (from the stopcock handle 14*c*) than the pressure-relief valve 20. Such design minimizes the opportunity to override and/or damage the pressure-relief valve 20, which may otherwise result in harm to the patient.

Figure 8:
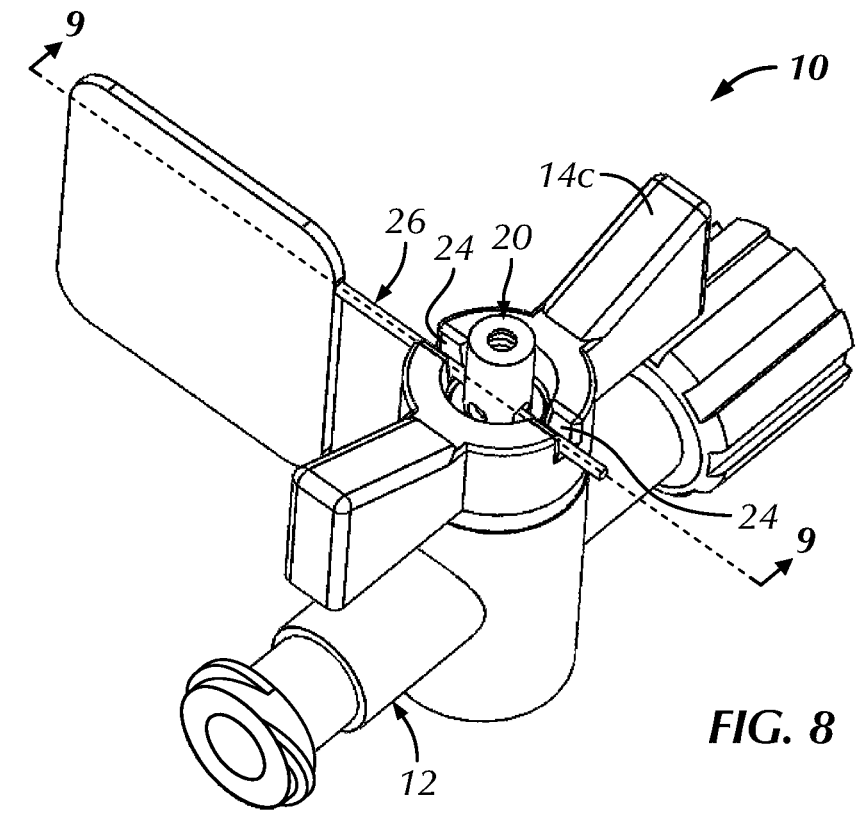
FIG. 8 is a perspective view of the inflation hub of FIG. 1 prior to use, with a release pin maintaining a pressure-relief valve thereof in an open configuration.
Figure 9:
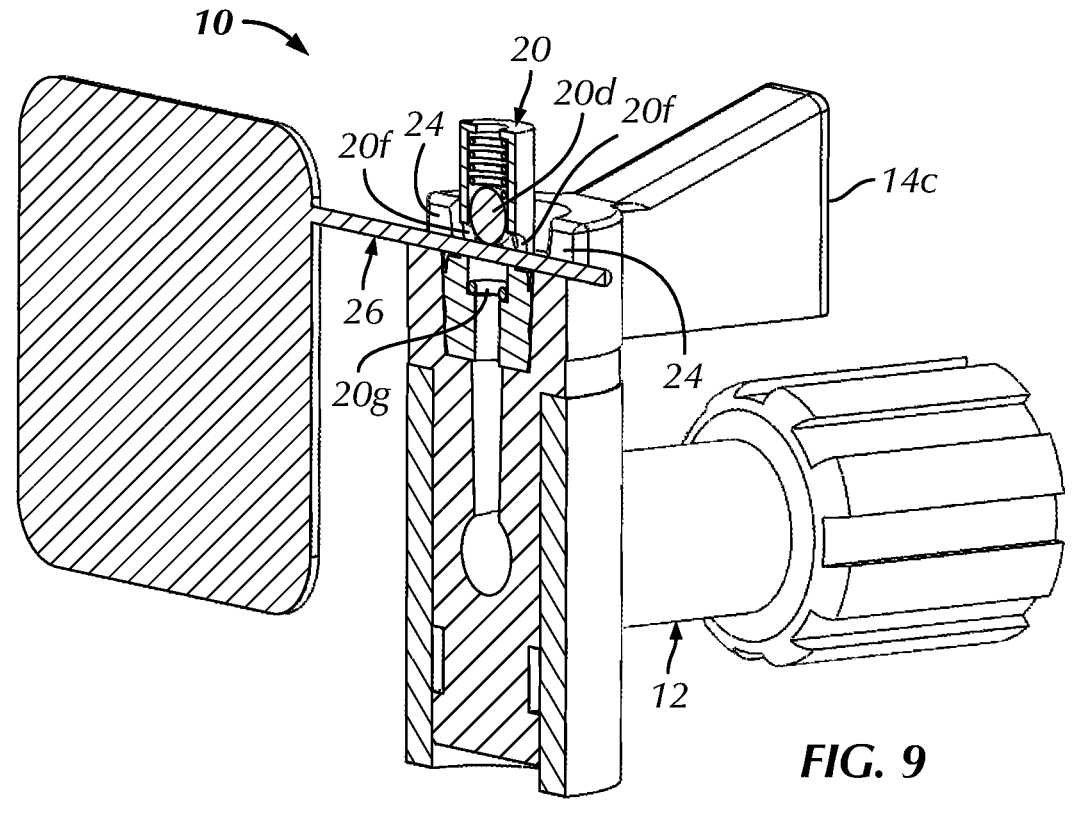
FIG. 9 is a cross-sectional perspective view of the inflation hub of FIG. 8, taken along sectional line 9-9 of FIG. 8.

In one configuration, as shown in FIGS. 8 and 9, the upper rim 22*b* of the socket 22 may include at least two coaxial/diametrically opposed recesses 24, in registry/aligned with two coaxial/diametrically opposed side vent ports 20*f*. Prior to use, a release pin 26 may extend through the opposed and aligned recesses 24 and side vent ports 20*f*, and maintain the valve member 20*d* biased and spaced away from the sealing member 20*g*, against the bias of the loading member 20*e*. That is, the valve member 20*d* and the loading member 20*e* may be supported upon the release pin 26 in a compressed state. In the illustrated embodiment, the release pin 26 includes a tabbed proximal end for simplified handling, but the disclosure is not so limited as the release pin 26 may take alternative configurations capable of performing the function of the release pin 26 described herein.

Advantageously, the release pin 26 lifts the valve member 20*d* off of the sealing member 20*g* so that the two components do not contact one another during transport and storage prior to use. Advantageously, such spacing prevents formation of stiction between the valve member 20*d* and the sealing member 20*g*, which may otherwise occur if the valve member 20*d* is biased against the sealing member 20*g* for an extended prior of time prior to use. As should be understood by those of ordinary skill in the art, when a valve's moving component, e.g., the valve member 20*d*, does not move for an extended period of time, it tends to stick in that position. Initially, therefore, additional pressure, greater than the normal cracking pressure thereof, becomes required to overcome the stiction. After the first actuation of the valve, the stiction is generally eliminated. Nevertheless, an increased cracking pressure of the pressure-relief valve 20, even for the first actuation of the valve 20, may expose the fluid inflatable apparatus to excess pressure and result in damage to the apparatus as well as the surrounding environment, such as, for example to a catheter 5 and the vessel receiving the catheter, thereby harming the patient.

In operation, the release pin 26 is removed, i.e., withdrawn, from the opposed and aligned recesses 24 and side vent ports 20*f* by the user prior to use of the inflation hub 10. When the release pin 26 is removed just before use, the valve member 20*d* is biased into contact with the sealing member 20*g* under the bias of the loading member 20*e* and seals the pressure-relief valve 20 in the closed position thereof, but does not stick because the components have not been touching for enough time to stick.

It will be appreciated by those skilled in the art that changes could be made to the embodiments described above without departing from the broad inventive concept thereof. For example, the inflation hub 10 is not limited to medical uses and may be designed and configured for operation with nearly any variety of valve in nearly any industry, wherein the combination of a shut-off valve and a pressure-relief valve to relieve pressure at a predetermined level is desirable, such as fluid transmission, fluid storage and related uses where pressure relief in potential over pressurization situations is desirable. It is understood, therefore, that this disclosure is not limited to the particular embodiments disclosed, but it is intended to cover modifications within the spirit and scope of the present disclosure, as set forth in the appended claims.

I claim:

1. An inflation hub for attachment to a fluid inflatable apparatus, the inflation hub comprising:
    a body having an internal lumen defining a first lumen section and a second lumen section, an inlet of the first lumen section being configured for connection to an inflation device, and an outlet of the second lumen section being configured for connection to the fluid inflatable apparatus;
    a stopcock valve having a stem angularly extending from a portion of the body between the first lumen section and the second lumen section of the internal lumen, the stem being selectively rotatable between an open position, wherein an internal channel of the stem fluidly connects the first lumen section with the second lumen section, and a closed position, wherein the stopcock valve fluidly disconnects the first lumen section from the second lumen section; and
    a pressure-relief valve integrated within the stem of the stopcock valve and in fluid communication with the internal channel thereof, the pressure-relief valve including a loading member biasing the pressure-relief valve into a closed position thereof, the pressure-relief valve being configured to move into an open position thereof when the stopcock valve is in the open position thereof and a pressure with the internal lumen of the body exceeds a threshold, opening pressure of the loading member,
    wherein the stem includes a sidewall terminating in an upper rim, the upper rim defining an open upper end of the stem and the sidewall having a recess extending therethrough, the recess being positioned downstream of the pressure-relief valve and configured to enable fluid escape therethrough irrespective of fluid escape through the open upper end of the stem.

2. The inflation hub of claim 1, wherein the stopcock valve further comprises a stopcock valve body angularly extending from the internal lumen of the body, and the stem is sealing and rotationally received within the valve body.

3. The inflation hub of claim 2, wherein the stopcock valve body is monolithic with the body.

4. The inflation hub of claim 1, wherein the internal channel of the stem has a generally lateral channel portion and a generally axial channel portion in fluid communication with and angularly extending therefrom.

5. The inflation hub of claim 4, wherein the generally lateral channel portion of the stem is interposed between, and in line with, the first lumen section and the second lumen section in the open position of the stopcock valve.

6. The inflation hub of claim 4, wherein the generally lateral channel portion of the stem is interposed between, and angularly offset from, the first lumen section and the second lumen section in the closed position of the stopcock valve.

7. The inflation hub of claim 1, wherein the stem of the stopcock valve is selectively rotatable between only two operative positions, the open position thereof being a first of the two operative positions and the closed position thereof being a second of the two operative positions.

8. The inflation hub of claim 1, wherein the stem of the stopcock valve is rotatable substantially 90° between the open position thereof and the closed position thereof.

9. The inflation hub of claim 1, wherein the pressure-relief valve further comprises:

a valve body sealingly mounted to the stem, the valve body having an internal valve body channel in fluid communication with the internal channel of the stem;

a valve seat within the internal valve body channel; and a movable valve member sealingly engaged with the valve seat by the loading member in the closed position of the pressure-relief valve.

10. The inflation hub of claim 9, wherein the valve body of the pressure-relief valve further includes at least one vent port fluidly communicating the internal valve body channel with external atmosphere, the at least one vent port being fluidly disconnected from the internal channel of the stem by the engagement of the movable valve member with the valve seat in the closed position of the pressure-relief valve and the at least one vent port being fluidly communicated with the internal channel of the stem in the open position of the pressure-relief valve.

11. The inflation hub of claim 9, wherein the valve member is a ball.

12. The inflation hub of claim 1, wherein the loading member is a spring.

13. The inflation hub of claim 1, wherein the threshold, opening pressure of the loading member is approximately 6 psi.

14. The inflation hub of claim 1, wherein the stopcock valve further includes a handle laterally extending from the stem, whereby rotation of the handle is configured rotate the stem.

15. The inflation hub of claim 1 in combination with a medical catheter, wherein the fluid inflatable apparatus is the medical catheter, the medical catheter including an inflatable occlusion balloon fluidly connected with a catheter shaft, the catheter shaft being selectively connectable with the outlet of the second lumen section.

16. The inflation hub of claim 1, wherein the pressure-relief valve extends beyond the upper rim of the stem of the stopcock valve.

17. A method of using the inflation hub of claim 1, the method comprising the steps of:

connecting the fluid inflatable apparatus with the outlet of the second lumen section; and inflating the fluid inflatable apparatus from the inlet of the first lumen section.

18. The method of claim 17, further comprising the step of:

rotating the stem into the open position thereof before the inflating step, thereby fluidly connecting the first lumen section with the second lumen section through the internal channel of the stem.

19. The method of claim 17, wherein the inflating step comprises inflating the fluid inflatable apparatus to a pressure greater than the threshold, opening pressure of the loading member, thereby moving the pressure-relief valve into the open position thereof.

20. The method of claim 17, further comprising the step of:

rotating the stem into the closed position thereof.

* * * * *